United States Patent [19]
Jasinski et al.

[11] 4,007,096
[45] Feb. 8, 1977

[54] TRACE GAS DETECTION METHOD
[75] Inventors: Raymond J. Jasinski; Isaac Trachtenberg, both of Dallas, Tex.
[73] Assignee: Texas Instruments Incorporated, Dallas, Tex.
[22] Filed: May 1, 1975
[21] Appl. No.: 573,666

Related U.S. Application Data
[62] Division of Ser. No. 370,898, June 18, 1973, Pat. No. 3,909,384.

[52] U.S. Cl. ................................ 204/1 T; 204/1 R
[51] Int. Cl.$^2$ ...................................... G01N 27/46
[58] Field of Search ....... 204/1 N, 1 Y, 1 T, 195 G, 204/195 M, 195 P

[56] References Cited
UNITED STATES PATENTS

| 3,622,487 | 11/1971 | Chand et al. | 204/195 P |
| 3,622,488 | 11/1971 | Chand et al. | 204/195 P |
| 3,709,813 | 1/1973 | Johnson et al. | 204/195 G |
| 3,776,832 | 12/1973 | Oswin et al. | 204/195 R |
| 3,821,090 | 6/1974 | Topol et al. | 204/1 N |
| 3,826,971 | 7/1974 | Jasinski et al. | 204/195 G |
| 3,835,009 | 9/1974 | Barna et al. | 204/195 G |

Primary Examiner—T. Tung
Attorney, Agent, or Firm—Harold Levine; James T. Comfort; William E. Hiller

[57] ABSTRACT

The disclosure relates to electro-chemical sensors for sensing gaseous nitrogen dioxide in the presence of carbon monoxide, oxygen, nitrogen, sulfur dioxide, nitric oxide and in chemically compatible mixtures of these gases as well as capable of sensing gaseous materials which are more strongly oxidizing than $NO_2$, the sensor being formed from an Fe-1173 glass. The disclosure also relates to an electro-chemical sensor formed from 15% manganese $As_2S_3$ glass which is capable of sensing gaseous materials which are more oxiding than $NO_2$ in the presence of $NO_2$, CO, $O_2$, $N_2$, $SO_2$, NO and in chemically compatible mixtures of these gases. The disclosure also includes apparatus for determining when $NO_2$ is being sensed rather than more strongly oxidizing gaseous materials by the simultaneous use of the Fe-1173 glass electro-chemical sensor and the sensor formed from 15% Mn-$As_2S_3$ glass.

10 Claims, 5 Drawing Figures

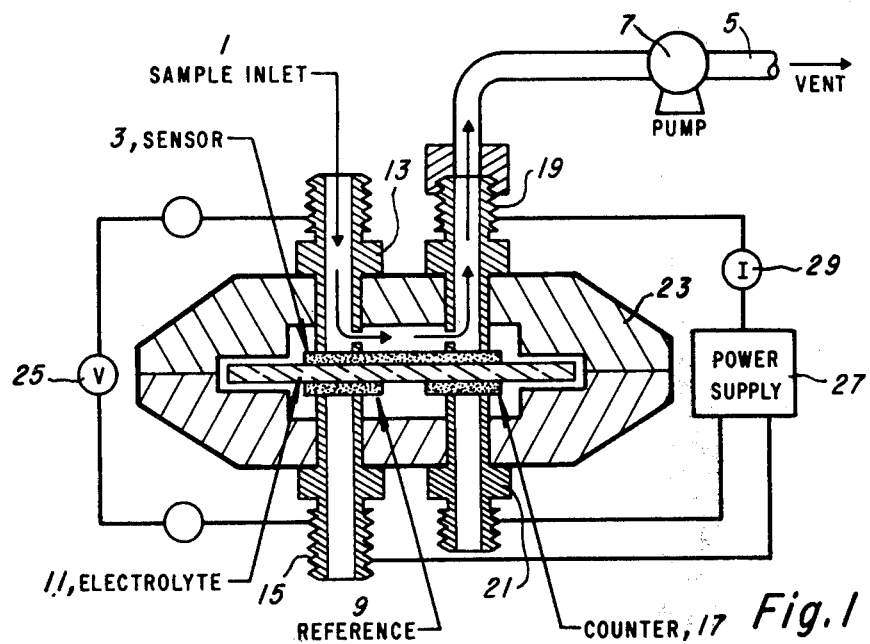
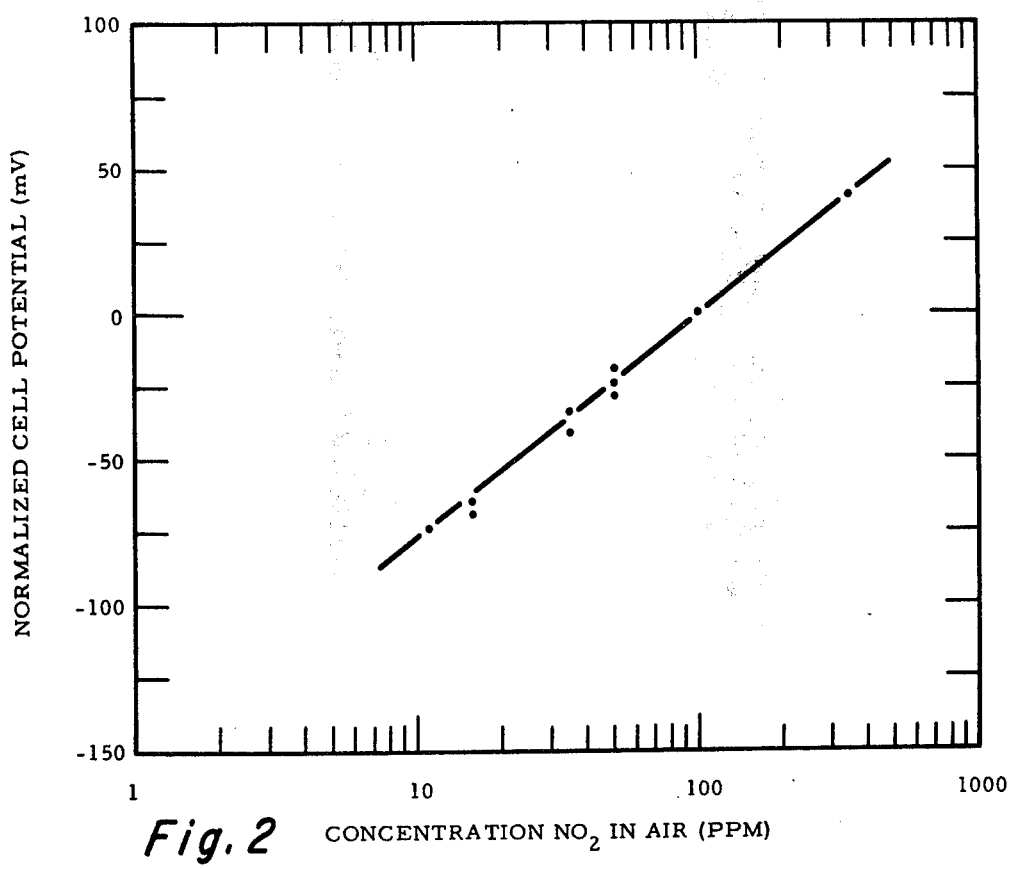

POTENTIAL CHANGES VERSUS GAS PHASE COMPOSITION

(RELATIVE TO POTENTIAL UNDER NITROGEN)

| GAS | GLASS | | |
|---|---|---|---|
| | Fe-1173 | MnO-$As_2S_3$ | 1173 |
| Air* | 0 mv | 0 mv | 10 mv |
| $NO_2$ (350 ppm) | 365 mv | 3 mv | 263 mv |
| $SO_2$ (100%) | 4 mv | 0 mv | −221 mv |
| CO (1%) | 2 mv | 0 mv | −90 mv |
| NO (100 ppm) | 2 mv | -- | -- |
| $H_2O_2$** (0.01%) | 54 mv | 80 mv | -- |
| $CH_4$ | 2 mv | -- | -- |

\* Key Points

\*\*In Solution

TRACE GAS DETECTION METHOD

This is a division of application Ser. No. 370,898, filed June 18, 1973, now U.S. Pat. No. 3,909,384, issued Sept. 30, 1975.

This invention relates to an electro-chemical gas sensor cell system capable of continuously monitoring gaseous pollutants in ambient urban air, stack gases from power plants, automobile exhausts and the like, to determine the presense of $NO_2$ as well as more strongly oxidizing gases, such as ozone, in the presence of CO, $O_2$, $N_2$, $SO_2$, NO and chemically compatible mixtures of these gases as well as a system for determining when $NO_2$ is the specific one of the gases being sensed.

There has been a general need for low cost equipment to continuously monitor gas pollutants in ambient urban air, in stack gases for power plants, in automobile exhausts and other pollution causing sources. In the past, this type of analysis has required going through the costly and slow procedure required by the standard textbooks wherein such gases are passed through a series of liquids to remove certain ones of the gases, one at a time, and determine qualitatively and quantitatively the gases present.

The prior art has also found difficulty in monitoring low concentrations of $NO_2$ and high oxidizing gases at concentrations of 0.01 to 0.1 parts per million by volume. Prior art electro-chemical sensors have also had an inherent lack of specificity, insufficient sensitivity to monitor urban air and have been of relatively high cost. Prior art electrochemical sensors have gained partial selectivity through the preliminary chemical treatment of the sample gas (selective diffusion through membranes).

In accordance with the present invention, there is provided an electro-chemical gas sensor cell system which is capable of which when a gas which is as oxidizing as $NO_2$, or more strongly oxidizing, is present in a gaseous atmosphere containing CO, $O_2$, $N_2$, $SO_2$, NO and chemically compatible mixtures of these gases, which is of relatively low cost, relatively high sensitivity and capable of specifically identifying $NO_2$ both qualitatively and quantitatively. There is also provided a relatively inexpensive electrochemical gas sensor which achieves its great selectivity through the inherent properties of the sensor material itself. In accordance with one embodiment of the invention, there is provided an electrochemical sensor whichh is composed of Fe-1173 glass, as will be explained in more detail hereinbelow, which is capable of providing a voltage between the sensor and a reference electrode which is separated from the sensor by an electrolyte to provide an output voltage which is linearly related to the logarithm of the concentration of $NO_2$ passing over the sensor.

In accordance with a second embodiment of the invention, the sensor is formed from 15% $Mn-As_2S_3$ glass which is 15 mole percent MnO fused into a substrate of arsenic trisulfide. This sensor will detect gases which are more strongly oxidizing than $NO_2$ but will not detect $NO_2$ in the same environment as discussed above.

In accordance with a third embodiment of the invention, a predetermined voltage is presented across the sensor and the reference electrode and a current is passed between the sensor and a counter electrode which is separated from the sensor electrode by the same electrolyte. In this case, the current passing through the sensor to the counter electrode has a direct linear relation to the amount of $NO_2$ gas or more strongly oxidizing gas such as ozone or the like passing across the sensor. In accordance with the third embodiment of the invention, the sensor is either that of the first or second embodiment.

In accordance with the fourth embodiment of the invention, an electro-chemical gas sensor cell in accordance with the first embodiment of the invention can be used in conjunction with an electro-chemical gas sensor cell in accordance with the second embodiment of the invention, whereby, if each of the sensor cells detects an oxidizing gas it can be determined that this gas is more strongly oxidizing than $NO_2$. If only the sensor cell in accordance with the first embodiment has detected an oxidizing gas whereas the second sensor cell does not, it is immediately determined that $NO_2$ is present in the example under test and no gas more strongly oxidizing than $NO_2$ is present.

It is therefore an object of this invention to provide a low cost electro-chemical gas sensor cell capable of detecting $NO_2$ and more oxidizing gases in the presence of CO, $O_2$, $N_2$, $SO_2$, NO and in chemically compatible mixtures of these gases.

It is a further object of this invention to provide an electro-chemical gas sensor cell capable of detecting gases more strongly oxidizing than NO in the presence of CO, $O_2$, $N_2$, $SO_2$, NO, and in chemically compatible mixtures of these gases.

It is a yet further object of this invention to provide an electro-chemical gas sensor cell system capable of determining specifically whether $NO_2$ specifically is present in a sample containing CO, $O_2$, $N_2$, $SO_2$, NO and chemically compatible mixtures of gases.

It is a still further object of this invention to provide an electro-chemical gas sensor formed from a chalcogenide glass having at most a small amount of crystalline structure and a resistivity of less than about ten thousand ohm-centimeters.

The above objects and still further objects of the invention will immediately become apparent to those skilled in the art after consideration of the following preferred embodiments thereof, which are provided by way of example and not by way of limitation wherein:

FIG. 1 is a schematic diagram of an electro-chemical gas sensor cell in accordance with the first and second embodiments of the present invention;

FIG. 2 is a graph of the voltage output across the sensor and reference electrode of the gas sensor of FIG. 1 in millivolts as compared with the logarithm of the concentration of $NO_2$ in air in parts per million;

Figure 3:
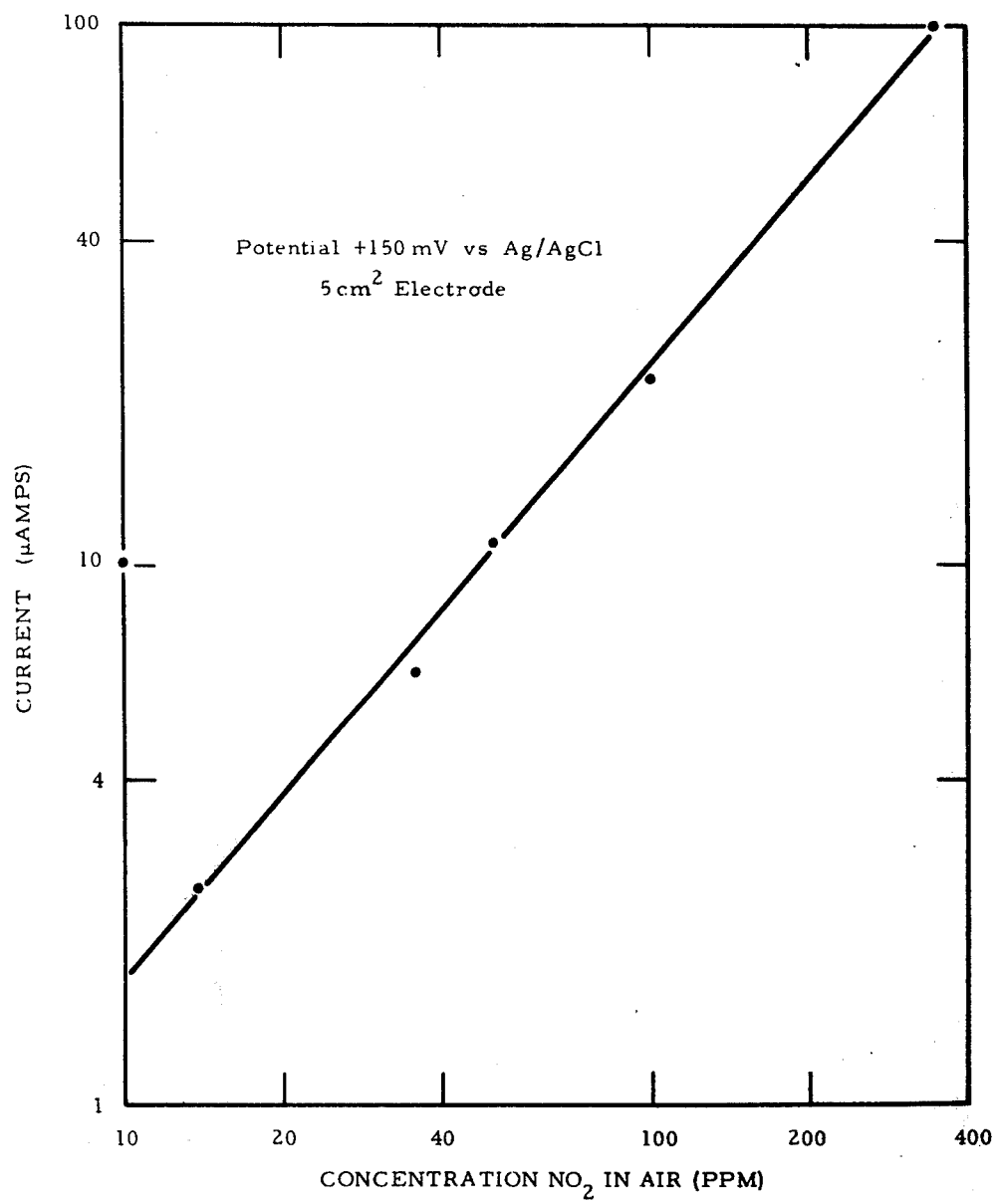
FIG. 3 is a graph of the output current across the sensor and counter electrode of FIG. 1 in microamps as compared with the concentration of $NO_2$ in air parts per million passing over the sensor.

Referring now to FIG. 1, there is shown an electro-chemical gas sensor cell in accordance with the first and second embodiments of the present invention. The sensor cell includes a sample inlet 1 for receiving a gas sample to be tested, the sample passing through the cell and over the sensor 3, the gas being drawn to the outlet vent 5 by means of a pump 7 which draws the sample through the cell. The sensor 3 is separted from a reference electrode 9 by an electrolyte 11, an electrically conductive cell housing portion 13 being electrically connected to the sensor 3 and a cell housing portion 15 being electrically connected to the reference electrode 9. The cell also includes a counter electrode 17 which is spaced from the sensor 3 and has an electrolyte 11 between the sensor 3 and the counter electrode 17. An electrically conducting housing portion 19 is connected to the sensor 3 and an electrically conducting housing portion 21 is connected to the counter electrode 17. Electrode 17 is only required when an output in accordance with FIG. 3 is desired. It can be seen that the gas flow will pass through the housing portion 13 which includes the sample inlet 1, over the sensor 3 and out to the outlet vent 5 through the housing portion 19. The housing portions 13, 15, 19 and 21 are secured within an electrically insulating housing member 23 in which the sensor 3, reference electrode 9, counter electrode 17 and electrolyte 11 are also positioned. separated The sensor 3 is formed from a chalcogenide glass, one embodiment thereof being an 1173 glass which has been doped with iron, cobalt, nickel or the selenides of iron, cobalt and nickel as impurities. The 1173 glass is fully set forth in the Journal of the Electro-Chemical Society, Volume 118, No. 4, April 1971, at pages 571–576. This article indicates that such glass in its undoped form comprises 60 mole percent selenium, 28 mole percent germanium and 12 percent antimony. The glass in accordance with this embodiment may have small amounts of crystalline structure and will include as much of the dopant as can possibly be added without the dopant appearing in the glass as the free metal. This will provide a resistivity in the range of $10^4$ ohm-centimeters to 50 ohm centimeters or less and preferably $10^3$ ohm-centimeter or less. It has been found that for an iron impurity in the glass, the weight range of the iron is in the range of 1 to 4%. No upper limit has yet been found for the other impurities listed above.

The iron glass is prepared by fusing the appropriate amount of iron wire at 900° to 1000° C. with the glass $Se_{60}Ge_{28}Sb_{12}$, previously synthesized directly from the pure elements and ground up. This provides the non-porous glass sensor required in accordance with the present invention. As will be explained in more detail hereinbelow, it has been found that the above described sensor will provide a response to $NO_2$ and gases more strongly oxidizing than $NO_2$, in the presence of CO, $O_2$, $N_2$, $SO_2$, NO and in chemically compatible mixtures of these gases.

In accordance with the second embodiment of the invention, the sensor 3 is formed from 15% $Mn$-$As_2S_3$ glass. Sensors formed from this glass have been found to be responsive in the manner to be described hereinbelow to gases which are more strongly oxidizing than $NO_2$, such as above, but not to $NO_2$.

The electrolyte 11 is impregnated or soaked into filter paper between the sensor 3 and the electrodes 9 and 17. The electrolyte material is not critical but it can be from concentrated nitric or sulfuric acids to potassium chloride which has a pH of 7, so it can be seen that almost any electrolyte can be utilized.

The counter electrode 17 and reference electrode 9 can be formed of standard materials, such as silver chloride on a silver screen, tantalum, or the like as is well known in the art. Examples of such electrodes are set forth in "Reference Electrodes", D. Ives and G. Janz, Academic Press, N.Y. 1961, with the proviso that the counter electrode material, on discharge, must not inject electro-active materials into the electrolyte.

It can be seen from the above that the sensor in accordance with the first embodiment will sense any gas which is as oxidizing as $NO_2$ or more strongly oxidizing but will not be selective, whereas the sensor in accordance with the second embodiment will only sense any gas which is more strongly oxidizing than $NO_2$ but again will not be selective. The sensing of these gases by the sensor 3 is accomplished in the following manners. Referring again to FIG. 1, there is shown a voltmeter 25 connected across the housing portions 13 and 15. This voltmeter will measure an increase in the voltage at the sensor 3 relative to the reference electrode 9 to determine whether one of the gases to which the sensor 3 is responsive is present in the sample being passed into the sample inlet 1 and out through the vent.

FIG. 2 is a graph of the output voltage of a normalized electro-chemical gas sensor cell as set forth in FIG. 1 in millivolts for various concentrations of $NO_2$ in air in parts per million. It can be seen that in the logarithmic graph set forth for the concentration of $NO_2$ in parts per million, the curve is linear. It has been found by experimentation that this curve actually extends downwardly to concentrations as low as one part per million and is still linear in that range and possibly below that range. It is therefore apparent that not only can the particular gases mentioned above be tested in accordance with this procedure in a qualitative manner but also in a quantitative manner by means of the calibration curve of FIG. 2.

In accordance with the second procedure for measuring the concentration of the gases under test, a voltage is placed across the sensor 3 and the reference electrode 9 and current is passed between the sensor 3 and the counter electrode 17 by means of a power supply 27 as shown in FIG. 1. The current passing between the sensor 3 and the counter electrode 17 is measured by the meter 29. A graph of the results of such measurement is shown in FIG. 3 where it is shown that a linear relationship exists between the current in microamps measured by the ammeter 29 and the concentration of $NO_2$ in air in parts per million. The graph in FIG. 3 was provided utilizing a potential across the sensor 3 and the reference electrode 9 of 150 millivolts with an Ag/AgCl 5 cm² electrode. Again, it is apparent that the gases under test can be measured both qualitatively as well as quantitatively in view of the calibration curve set forth in FIG. 3.

Figures 4, 5:
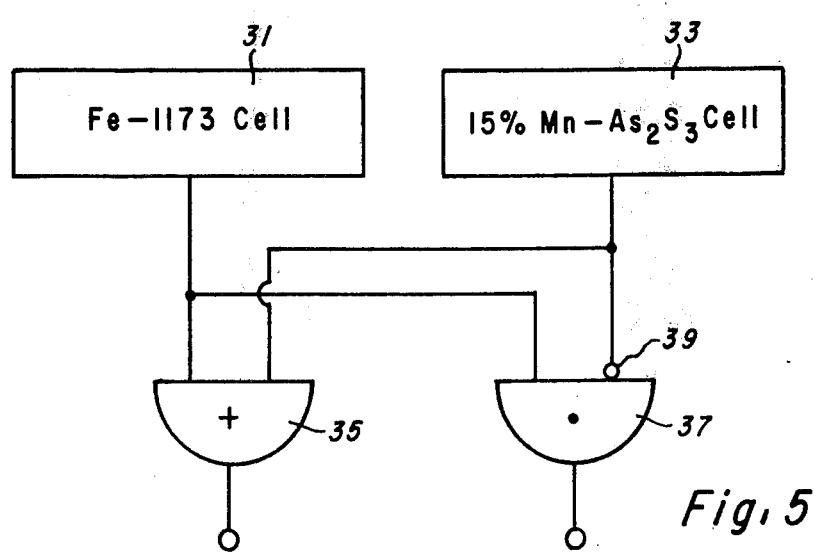
FIG. 4 is a chart showing the voltage sensed at the meter across the sensor and reference electrode of FIG. 1 for various gases passed over the sensor and for various sensors.
FIG. 5 is a circuit diagram depicting the third embodiment of the present invention.

Referring now to FIG. 4, there is shown a graph of potential changes across the sensor vs. gas phase composition. Three types of gas sensors of the type described above are utilized, one being the Fe-1173 of the first embodiment, the second being the $Mn$-$As_2S_3$ of the second embodiment and the third being undoped 1173 glass which gave no meaningful results whereas when doped with iron there was a significant change in voltage for $NO_2$ and for a 0.01% hydrogen peroxide solution. In the case of the manganese oxide arsenic trisulfide glass, the only significant change in voltage appears for the hydrogen peroxide in solution, this material being more strongly oxidizing than $NO_2$. The effectiveness of the sensors in accordance with the present invention is therefore demonstrated by this chart.

In view of the ability of the iron doped glass to sense $NO_2$ as well as more strongly oxidizing gases whereas the manganese oxide - arsenic trisulfide glass is merely capable of sensing gases which are more strongly oxidizing than $NO_2$, the use of two sensors, one using an iron 1173 glass and the other using a manganese oxide - arsenic trisulfide glass can be utilized together to indicate whether the gas being sensed is specifically $NO_2$ or some other gas. In FIG. 5, the box 31 is an electro-chemical gas sensing cell of FIG. 1 using an Fe-1173 sensor whereas box 33 is an electro-chemical gas sensor cell as set forth in FIG. 1 using a manganese ozide-arsenic trisulfide glass sensor. An output provided from each of the sensors which can be the output voltage sensed by the voltmeter of FIG. 1 is passed to an OR gate 35 as well as an AND gate 37 having an inhibit electrode 39. It can be seen that OR gate 35 will provide a positive output signal if either cell 31 or cell 33 senses a gas to which it is responsive. Therefore a proper output from OR gate 35 will indicate that $NO_2$ or a more strongly oxidizing gas is present. AND gate 37 will provide an output only if a gas to which cell 31 is responsive is present and if a gas to which cell 3 is responsive is not present. Therefore, an output from AND gate 37 is only present when $NO_2$ specifically has been sensed since if a more strongly oxidizing gas were present, there would be an output signal from both of the cells 31 and 33. It is therefore apparent that the embodiment of FIG. 5 provides a method of specifically determining the presence of $NO_2$ relative to the more strongly oxidizing gases which would also operate any one of the cells described herein.

Electrodes 3 of the first embodiment were formed by grinding the iron doped 1173 glass, mixing it with polytetrafluoroethylene (Teflon) emulsion and placing the mixture on a tantalum screen. This was placed in an oven with air therein at 290° C. for 3 to 5 minutes to remove any wetting agent and allow the polytetrafluoroethylene to flow and bond to the screen. This sensor electrode 3 was used in a cell having an electrolyte 11 of in KCl, pH 2 soaked into fiber glass filter paper with the reference electrode 9 and the counter electrode of 17 being made silver chloride on a silver screen. The silver-silver chloride screen could be replaced by a tantalum screen. The same electrolyte, reference electrode and counter electrode were also used with the sensor of the second embodiment.

Though the invention has been described with respect to specific preferred embodiments thereof, many variations and modifications will immediately become apparent to those skilled in the art. It is therefore the intention that the appended claims be interpreted as broadly as possible in view of the prior art to include all such variations and modifications.

What is claimed is:

1. A method of detecting the presence of gaseous $NO_2$ and more strongly oxidizing gases in a gaseous atmosphere including at least one gas taken from the group consisting of CO, $O_2$, $N_2$, $SO_2$, NO and chemically compatible mixtures of these gases, said method comprising:

providing an electro-chemical gas sensing cell including a sensor formed of a doped chalcogenide glass consisting of about 60 mole percent selenium, 28 mole percent germanium, 12 mole percent antimony and containing as a dopant about 1% to about 4% by weight of iron, an electrolyte contacting a side of said sensor, and a reference electrode contacting said electrolyte, exposing the doped chalcogenide glass sensor on the side opposite to said electrolyte — contacting side to a sample of the gaseous atmosphere, and measuring the electrical signal developed by the cell in response to the exposure of the doped chalcogenide glass sensor to the gas sample.

2. A method as set forth in claim 1, further including providing a predetermined electrical potential across the doped chalcogenide glass sensor and the reference electrode, passing an electrical current between the doped chalcogenide glass sensor and a second electrode, and measuring the electrical current passing between the doped chalcogenide glass sensor and the second electrode as the doped chalcogenide glass sensor is being exposed to the gas sample.

3. A method of detecting the presence of more strongly oxidizing gases than gaseous $NO_2$ in a gaseous atmosphere including at least one gas taken from the group consisting of CO, $O_2$, $N_2$, $SO_2$, NO and chemically compatible mixtures of these gases, said method comprising:

providing an electro-chemical gas sensing cell including a sensor formed of a doped chalcogenide glass consisting of 15% $MnAs_2S_3$, an electrolyte contacting a side of said sensor, and a reference electrode contacting said electrolyte, exposing the doped chalcogenide glass sensor on the side opposite to said electrolyte — contacting side to a sample of the gaseous atmosphere, and measuring the electrical signal developed by the cell in response to the exposure of the doped chalcogenide glass sensor to the gas sample.

4. A method as set forth in claim 3, further including providing a predetermined electrical potential across the doped chalcogenide glass sensor and the reference electrode, passing an electrical current between the doped chalcogenide glass sensor and a second electrode, and measuring the electrical current passing between the doped chalcogenide glass sensor and the second electrode as the doped chalcogenide glass sensor is being exposed to the gas sample.

5. A method of detecting the presence of gaseous $NO_2$ and more strongly oxidizing gases in a gaseous atmosphere including at least one gas taken from the group consisting of CO, $O_2$, $N_2$, $SO_2$, NO and chemically compatible mixtures of these gases, said method comprising:

providing a first electro-chemical gas sensing cell including a doped chalcogenide glass sensor of about 60 mole percent selenium, 28 mole percent germanium, 12 mole percent antimony and containing as a dopant about 1% to about 4% by weight of iron, an electrolyte contacting a side of said sensor, and a reference electrode contacting said electrolyte for producing an electrical signal from said first cell representative of the presence of gaseous $NO_2$ and more strongly oxidizing gases in response to the exposure of the doped chalcogenide glass of said first cell to a sample of the gaseous atmosphere, providing a second electro-chemical gas sensing cell including a doped chalcogenide glass sensor of 15% $MnAs_2S_3$, an electrolyte contacting a side of said sensor, and a reference electrode contacting said electrolyte for producing an electrical signal from said second cell representative of the presence of more strongly oxidizing gases than $NO_2$ in response to the exposure of the doped chalcogenide glass sensor of said second cell to the same gas sample, exposing the respective doped chalcogenide glass sensors of said first and second electro-chemical sensing cells on the sides opposite to said electrolyte — contacting sides to a sample of the gaseous atmosphere, measuring the respective electrical signal developed by said first and second cells in response to the exposure of the doped chalcogenide glass sensors thereof to the gas sample, and determining from the presence or absence of electrical signals developed by said first and second cells whether $NO_2$ and more strongly oxidizing gases are present in the gas sample.

6. A method of detecting the presence of gaseous $NO_2$ and more strongly oxidizing gases in a gaseous atmosphere including at least one gas taken from the group consisting of CO, $O_2$, $N_2$, $SO_2$, NO and chemically compatible mixtures of these gases, said method comprising:

providing an electro-chemical gas sensing cell including a doped chalcogenide glass consisting of about 60 mole percent selenium, 28 mole percent germanium, 12 mole percent antimony and containing as a dopant about 1% to about 4% by weight of iron, an electrical conductor connected to one side of said glass, an electrolyte material contacting the other side of said glass, and a reference electrode contacting said electrolyte material, exposing said one side of said glass to a sample of the gaseous atmosphere, and measuring the electrical signal developed by the cell in response to the exposure of said one side of said glass to the gas sample.

7. A method as set forth in claim 6, further including providing a pre-determined electrical potential across said glass and said spaced apart reference electrode included in the electrochemical gas sensing cell, passing an electrical current between said glass and a second spaced apart electrode of the electro-chemical gas sensing cell, wherein said glass, the reference electrode, and the second electrode are spaced from each other but in engagement with said electrolyte material, and measuring the electrical current passing between said glass and said the second electrode as said glass is being exposed to the gas sample.

8. A method of detecting the presence of more strongly oxidizing gases than gaseous $NO_2$ in a gaseous atmosphere including at least one gas taken from the group consisting of CO, $O_2$, $N_2$, $SO_2$, NO and chemically compatible mixtures of these gases, said method comprising:

providing an electro-chemical gas sensing cell including a chalcogenide glass consisting of 15% $MnAS_2S_3$, an electrical conductor connected to one side of said glass, an electrolyte material contacting the other side of said glass, and a reference electrode contacting said electrolyte material, exposing said one side of said glass to a sample of the gaseous atmosphere, and measuring the electrical signal developed by the cell in response to the exposure of said one side of said glass to the gas sample.

9. A method as set forth in claim 8 further including providing a pre-determined electrical potential across said glass and said spaced apart reference electrode included in the electro-chemical gas sensing cell, passing an electrical current between said glass and a second spaced apart electrode of the electro-chemical gas sensing cell, wherein said glass, the reference electrode, and the second electrode are spaced from each other but in engagement with the electrolyte material, and measuring the electrical current passing between the said glass and the second electrode as said glass is being exposed to the gas sample.

10. A method of detecting the presence of gaseous $NO_2$ and more strongly oxidizing gases in a gaseous atmosphere including at least one gas taken from the group consisting of CO, $O_2$, $N_2$, $SO_2$, NO and chemically compatible mixtures of these gases, said method comprising:

providing a first electro-chemical gas sensing cell including a chalcogenide glass of about 60 mole percent selenium, 28 mole percent germanium, 12 mole percent antimony and containing as a dopant about 1% to about 4% by weight of iron, an electrical conductor connected to one side of said glass, an electrolyte material contacting the other side of said glass, and a reference electrode contacting said electrolyte material for producing an electrical signal from said first cell representative of the presence of gaseous $NO_2$ and more strongly oxidizing gases in response to the exposure of said one side of said glass of the first cell to a sample of the gaseous atmosphere, providing a second electro-chemical gas sensing cell including a chalcogenide glass of 15% $MnAs_2S_3$, an electrical conductor connected to one side of said glass, an electrolyte material contacting the other side of said glass, and a reference electrode contacting said electrolyte material for producing an electrical signal from said second cell representative of the presence of more strongly oxidizing gases than $NO_2$ in response to the exposure to said one side of said chalcogenide glass of said second cell to the same gas sample, exposing said one sides of the respective glasses of the said first and the said second electro-chemical sensing cells to a sample of the gaseous atmosphere, measuring the respective electrical signals developed by said first and second cells in response to the exposure of said one side of the respective chalcogenide glasses thereof to the gas sample, and determining from the presence or absence of electrical signals developed by said first and second cells whether $NO_2$ and more strongly oxidizing gases are present in the gas sample.

* * * * *